United States Patent [19]
Bauer et al.

[11] Patent Number: 6,153,752
[45] Date of Patent: Nov. 28, 2000

[54] PROCESS FOR PREPARING HETEROCYCLES

[75] Inventors: Frank Bauer, Bonn, Germany; Chitoor Subramaniam, East Brunswick, N.J.

[73] Assignee: Creanova, Inc., Piscataway, N.J.

[21] Appl. No.: 09/494,258

[22] Filed: Jan. 28, 2000

[51] Int. Cl.$^7$ ............... C07D 239/26; C07D 231/12; C07D 261/18; C07D 261/12

[52] U.S. Cl. ............ 544/335; 544/242; 544/316; 544/318; 544/330; 544/332; 548/243; 548/247; 548/248; 548/374.1; 548/375.1

[58] Field of Search ................... 544/335, 242, 544/316, 318, 330, 332; 548/243, 247, 248, 374.1, 375.1

[56] References Cited

U.S. PATENT DOCUMENTS 4,808,595  2/1989  Hoffman ................... 544/362

*Primary Examiner*—John M. Ford
*Attorney, Agent, or Firm*—Abelman, Frayne & Schwab

[57] ABSTRACT

Process for the preparation of heterocycles by reacting 2-substituted acetals of malondialdehyde with a reactant selected from hydroxylamines and their salts, hydrazines and their salts, formamid, amidines and their salts, guanidines and their salts, aminoguanidines and their salts, nitroguanidine and their salts, O-alkyl-isoureas and their salts, O-cycloalkyl-isoureas and their salts, O-aralkyl-isoureas and their salts, O-aryl-isoureas and their salts, S-alkyl-isothioureas, S-cycloalkyl-isothioureas, S-aralkyl-isothioureas, S-arylisothioureas, S-alkyl-isothiouronium salts, S-cycloalkyl-isothiouronium salts, S-aralkyl-isothiouronium salts, S-aryl-isothiuronium salts, thiourea and urea.

17 Claims, No Drawings

PROCESS FOR PREPARING HETEROCYCLES

FIELD OF THE INVENTION

The present invention relates to a process for preparing heterocycles from 2-substituted and 2,2-disubstituted acetals of malondialdehyde.

DESCRIPTION OF THE BACKGROUND

Pyrazoles, isoxazoles and pyrimidines of general formula I, II, III, and IV

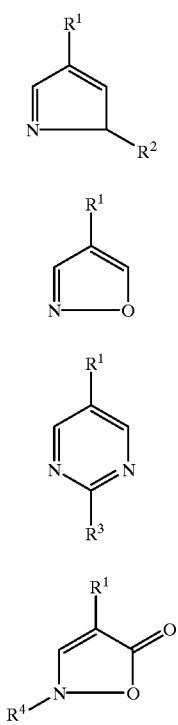

in which $R^1$ represents COOH, COONa, COOR, CHO, $C(OR)_2$, CN, $CONH_2$, CONHR or $CONR_2$, in which $R^2$ represents H, an alkyl-, cycloalkyl, aralkyl- or aryl-group with up to 12 carbon atoms, COOR, $CONH_2$, CONHR, $CONR_2$, alkyl-OH, cycloalkyl-OH, aralkyl-OH, aryl-OH, alkyl-OR, cycloalkyl-OR, aralkyl-OR and aryl-OR, in which $R^3$ represents H, an alkyl-, cycloalkyl-, aralkyl- or aryl-group with up to 12 carbon atoms, OH, OR, SH, SR, $NH_2$, NHR and $NR_2$, $NHNO_2$, $NHNH_2$, NHNHR, $NHNR_2$, COOR, $CONH_2$, CONHR, $CONR_2$, in which $R^4$ represents an alkyl-, cycloalkyl-, aralkyl- or aryl-group with up to 12 carbon atoms are important intermediates in the manufacture of pharmaceuticals and agrochemicals. (R's independently of each other represent alkyl-, cycloalkyl, aryl-aralkyl-groups.)

The compounds of the present invention can be synthesized according to principally known procedures by condensing 2-substituted 1,3-dialdehydes of the general formula (V)

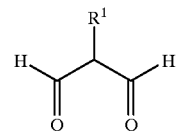

in which $R^1$ represents H, an alkyl-, cycloalkyl-, aralkyl-, aryl-group, COOH, COONa, COOR, CHO, $C(OR)_2$, CN, $CONH_2$, CONHR or $CONR_2$, with reagents such as hydroxylamines and their salts, hydrazines and their salts, formamid, amidines and their salts, guanidines and their salts, aminoguanidines and their salts, nitroguanidine and their salts, O-alkyl-isoureas and their salts, O-cycloalkyl-isoureas and their salts, O-aralkyl-isoureas and their salts, O-aryl-isoureas and their salts, S-alkyl-isothioureas, S-cycloalkyl-isothioureas, S-aralkyl-isothioureas, S-arylisothioureas, S-alkyl-isothiouronium salts, S-cycloalkyl-isothiouronium salts, S-aralkyl-isothiouronium salts, S-aryl-isothiuronium salts, thiourea and urea, respectively (JP 61,289,077; Schenone, P., Sansebastiano, L., Mosti, L., *J. Heterocycl. Chem.* 1990, 27 (2), 295; Holzer, W., Seiringer, G., *J. Heterocycl. Chem.* 1993, 30, 865; Kusumi, T. et al., *Tetrahedron Letters* 22 (1981), 36, 3451; Prelog, V., Wuersch, J., Koenigsbacher, K., *Helv. Chim. Acta* 1951, 34, 258; U.S. Pat. No. 4,808,595; Genin, M., J. et al. *J. Med. Chem.* 1998, 41; Reichardt, G., Kermer, W. D., *Synthesis* 1970, 538).

While the substituted malondialdehydes of general formula V normally are more stable toward polymerization than the unsubstituted malondialdehyde, they are thermally unstable as indicated, for example, by losses of 41% on distillation of ethoxycarbonyl-malondialdehyde under very mild conditions (Bertz, S. H., Dabbagh, G., Cotte, *J. Org. Chem.* 1982, 47, 2216). Handling-hazards and product losses, as well as a potential contamination of the reaction mixtures with polymeric material result from using the compounds of general formula II for the synthesis of heterocycles. Besides, the compounds of general formula I can be stored even above room temperature for extended periods of time.

Another disadvantage of synthesizing the compounds of general formula I, II, III and IV from the compounds of formula V is their limited availability. Production of the substituted aldehydes of general formula V from readily available starting materials generally requires several steps and the use of reagents that are difficult to handle under commercial conditions, such as NaH or CO. Besides, significant amounts of salt-waste are normally associated with the production of the compounds of general formula V. Consequently, a need existed for a process that allows for a production of the compounds of general formula I, II, III and IV from stable, easily available starting materials.

SUMMARY OF THE INVENTION

It is an object of the present invention to provide a process for preparing heterocycles from 2-substituted acetals of malondialdehyde of general formula VI:

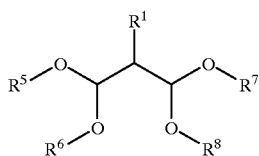

in which $R^1$ represents COOH, COONa, COOR, CHO, $C(OR)_2$, CN, $CONH_2$, CONHR or $CONR_2$, in which $R^5$, $R^6$, $R^7$ and $R^8$ are the same or different alkyl-, cycloalkyl-, aralkyl- or aryl-groups with up to 12 carbon atoms.

DETAILED DESCRIPTION OF THE PREFERRED EMBODIMENTS

The present invention provides a process for preparing heterocycles from 2-substituted acetals of malondialdehyde of general formula VI:

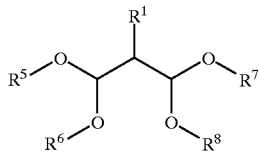

in which $R^1$ represents COOH, COONa, COOR, CHO, $C(OR)_2$, CN, $CONH_2$, CONHR or $CONR_2$, in which $R^5$, $R^6$, $R^7$ and $R^8$ are the same or different alkyl-, cycloalkyl-, aralkyl- or aryl-groups with up to 12 carbon atoms.

The compounds of general formula VI are easily accessible in accordance with the disclosure of an application filed on even date herewith entitled "Process for Preparing Substituted Acetals of Malondialdehyde", the disclosure of which is incorporated herein by reference.

It was found that the compounds of general formula VI can be reacted with one or several reactants such as hydroxylamines and their salts, hydrazines and their salts, formamid, amidines and their salts, guanidines and their salts, aminoguanidines and their salts, nitroguanidine and their salts, O-alkyl-isoureas and their salts, O-cycloalkyl-isoureas and their salts, O-aralkyl-isoureas and their salts, O-aryl-isoureas and their salts, S-alkyl-isothioureas, S-cycloalkyl-isothioureas, S-aralkyl-isothioureas, S-arylisothioureas, S-alkyl-isothiouronium salts, S-cycloalkyl-isothiouronium salts, S-aralkyl-isothiouronium salts, S-aryl-isothiuronium salts, thiourea and urea, respectively to form the heterocycles of general formula I, II, III and IV.

For example, methyl-1-phenyl-pyrazole-4-carboxylate could be prepared in a simple manner by reacting 3,3-dimethoxy-2-dimethoxymethyl-propionate and hydrazine-hydrochloride in the presence of aqueous HCl. Whereas, the presence of at least catalytic amounts of water in the reaction mixture is not absolutely necessary, it turned out advantageous in many cases. The addition of a catalyst, preferably an acidic catalyst like HCl, $H_2SO_4$, acidic montmorillonites or acidic ion exchange resins generally turned out to be advantageous with respect to a reduction of the reaction times, as well as, a stabilization of the products. The hydroxylamines, hydrazines, guanidines, aminoguanidines, nitroguanidines, isothioureas and amidines are often stabilized in the form of salts such as hydrochlorides. Since acidic reaction conditions were found advantageous, these reactants are preferentially used in their stabilized form. In a preferred embodiment of the process according to the invention, a heterogeneous catalyst, preferably an acidic heterogeneous catalyst, is used, especially with the process being carried out continuously. Despite the addition of acidic catalysts, the observed reaction rates were sometimes relatively low and, therefore, unacceptable in view of a commercialization. Especially in the cases where the reaction mixtures (initially) consisted of several phases, only low conversions could be achieved even after reaction times of 5 hours at 20° C. for example. Principally, there is the option of increasing the temperature in order to improve the reaction rates and, in fact, improved rates could be achieved by this means. However, reacting the compounds of general formula VI with one or several reactants in the presence of water and optionally an acid was found to normally give lowered yields and an increased amount of byproducts if the reaction temperatures were raised to temperatures substantially higher than 60° C.

Increased or even drastically increased reaction rates for the formation of the compounds of general formula I, II, III and IV in the presence of water were observed if the reaction was carried out in the presence of a co-solvent. Besides, higher yields and improved purities could be achieved.

The addition of a catalyst, preferably an acidic catalyst, is still advantageous. Under preferred conditions of the process according to the invention, the reaction is, therefore, carried out by mixing the compounds of general formula VI, at least catalytic amounts of water, a suitable co-solvent and an acidic catalyst.

Polar co-solvents like ethers, cyclic ethers, polyethylenglycol ethers, dialkyl amides or DMSO turned out to be especially advantageous. Ideally, the co-solvent or the mixture of co-solvents does not at all react with any component of the reaction mixture. In the case that the heterocycles of general formula I, II, III and IV are relatively polar, these products themselves can be used as the co-solvent.

However, the addition of a co-solvent is only advantageous if, otherwise, the reaction is slow, i. e. normally if the (initial) reaction mixture comprises of several phases. Otherwise, the co-solvent reduces the space-time-yield, besides having to be removed after the reaction in any case. If high temperatures, i. e. substantially higher than 60° C. are required, the addition of water can potentially lead to a hydrolysis respective decomposition of the groups $R^1$.

Further increased reaction rates were observed if the respective alcohols of general formula $R^5OH$, $R^6OH$, $R^7OH$ and $R^8OH$ were being removed during the reaction, preferably by distillation, with continuous distillation being especially preferred.

In order to allow for the safe removal of the heat of reaction under commercial conditions, the starting material or one or several reactants, i. e. the compounds of general formula VI, the optionally added water or the other reactants, can be fed to the remaining components of the reaction mixture. Whereas, it principally does not matter which of the components of the reaction mixture are being fed, at least in the case where the starting materials of general formula VI were relatively unpolar, improved rates were observed if these starting materials were fed to the remaining components of the reaction mixture. Accordingly, in a preferred embodiment of the process according to the invention, the compounds of general formula VI are being fed to the remaining components of the reaction mixture.

The process according to the invention can be carried out within a broad temperature range, which is only limited by the physical properties of the reaction mixture and the potential decomposition of starting materials and/or products at elevated temperatures. In the case where the boiling point would be exceeded under one atmosphere, the reaction can be carried out under pressure.

Although, the process according to the invention can be carried out at high temperatures, for example 180° C., it is a special advantage that relatively high reaction rates and conversions can be achieved under mild conditions, for example, at room temperature. By allowing for the reaction to be carried out at relatively low temperatures, improved selectivities resulted, as compared to the reaction being carried out at higher temperatures.

The process according to the invention can be carried out batch-wise, as well as continuously. In a preferred embodiment according to the invention, it is carried out continuously.

On hydrolysis of the compounds of general formula VI to the referring free aldehydes, it is normally advantageous to avoid the generation of a mixture of alcohols. In a preferred embodiment of the process of the invention, the groups $R^5$, $R^6$, $R^7$ and $R^8$ are therefore identical.

The products of general formula I, II, III, and IV can be isolated by standard techniques, for example by crystallization, distillation, etc. In the case of basic products, their isolation as a protonated salt, for example as a hydrochloride, turned to give material of exceptionally high purity in a simple manner. For example, methyl-4-pyrazole-carboxylate-hydrochloride could be isolated in high yields by evaporation of the reaction mixture to dryness and re-crystallization of the residue from THF.

Having described the present invention, references will now be made to certain examples, which are provided solely for purposes of illustration and are not intended to be limitative.

EXAMPLE 1

Methyl-Pyrazole-4-carboxylate-hydrochloride

To a stirred mixture of 9.92 g DI-water, 80.0 g THF, 0.88 g concentrated aqueous HCl and 6.18 g $N_2H_4$ * HCl were added 20.00 g 3,3-dimethoxy-2-dimethoxymethyl-propionate. The mixture was heated to 50° C. for 3.0 hours, and afterwards, cooled to room temperature. A GC-analysis of the reaction mixture revealed a total conversion of the 3,3-dimethoxy-2-dimethoxymethyl-propionate. The volatile components of the reaction mixture were removed by evaporation at 45° C./18 mm Hg, and the residue was subsequently re-crystallized from THF. By this means 9.56 g (65.7% of theory based on 3,3-dimethoxy-2-dimethoxymethyl-propionate) of white methyl-4-pyrazole-carboxylate-hydrochloride were isolated. Examination of the product by $^1$H- and $^{13}$C-NMR-spectroscopy gave no hints of any kind of impurities except for traces of pyrazole-4-carboxylate-hydrochloride. The mother liquor still contained substantial amounts of pyrazole-4-carboxylate-hydrochloride, as well as, methyl-pyrazole-4-carboxylate-hydrochloride.

EXAMPLE 2

Methyl-pyrazole4-carboxylate-hydrochloride

The procedure of example 1 was followed except that no THF was added to the reaction mixture. In order to achieve complete conversion of the 3,3-dimethoxy-2-dimethoxymethyl-propionate, it was necessary to heat the mixture to 60° C. for 4.0 hours. Isolation of the product, as described in example 1, gave 8.62 g methyl-pyrazole-4-carboxylate-hydrochloride (59.2% of theory based on 3,3-dimethoxy-2-dimethoxymethyl-propionate). The mother liquor contained substantial amounts of pyrazole-4-carboxylate-hydrochloride, as well as, methyl-pyrazole-4-carboxylate-hydrochloride.

EXAMPLE 3

Methyl-pyrazole-4-carboxylate-hydrochloride

The procedure of example 1 was followed, except during the reaction, a mixture of methanol, water, and THF was removed by vacuum distillation using a fractionation column. According to a GC-analysis of the reaction mixture, a full conversion of the 3,3-dimethoxy-2-dimethoxymethyl-propionate was achieved after a reaction time of only 2.5 hours. Methyl-pyrazole-4-carboxylate-hydrochloride could be isolated from the reaction mixture in 70.9% yield based on to 3,3-dimethoxy-2-dimethoxymethyl-propionate. The mother liquor contained substantial amounts of pyrazole-4-carboxylate-hydrochloride, as well as, methyl-pyrazole-4-carboxylate-hydrochloride.

EXAMPLE 4

Methyl-1-methyl-4-pyrazole-carboxylate

A stirred mixture of 1.12 g DI-water, 5.92 g concentrated aqueous HCl and 2.08 g $NH_2$-$NHCH_3$ was cooled to 15° C. and 10.00 g 3,3-dimethoxy-2-dimethoxymethyl-propionate were fed within 5 minutes. The mixture was stirred at 15° C. to 20° C. for 2.0 hours and, afterwards, approximately two-thirds of the solvent was removed in vacuo. The precipitated crystalline product was removed by suction-filtration, washed with a small amount of ice water and subsequently dried in vacuo. By this means, 4.00 g (63% of theory based on 3,3-dimethoxy-2-dimethoxymethyl-propionate) methyl-1-methyl4-pyrazole-carboxylate could be isolated. Identification of the product was based on $^1$H-NMR-, $^{13}$C- and IR-spectra. The mother liquor still contained methyl-1-methyl-4-pyrazole-carboxylate.

EXAMPLE 5

Methyl-1-phenyl-4-pyrazole-carboxylate

A stirred mixture of 2.27 g DI-water, 4.28 g concentrated aqueous HCl and 4.88 g $NH_2$-NHPh was cooled to 15° C. and 10.00 g 3,3-dimethoxy-2-dimethoxymethyl-propionate were fed within 5 minutes. The mixture was stirred at 20° C. for 3.0 hours and at 40° C. for 2 hours. After cooling to room temperature, 6.37 g (70% of theory based on 3,3-dimethoxy-2-dimethoxymethyl-propionate) of methyl-1-phenyl-pyrazole-4-carboxylate were isolated as described in example 4. Identification of the product was based on $^1$H-NMR-, $^{13}$C- and IR-spectra. The mother liquor still contained methyl-1-phenyl-4-pyrazole-carboxylate.

EXAMPLE 6

Methyl-1-phenyl-4-pyrazole-carboxylate

A stirred mixture of 2.27 g DI-water, 4.28 g concentrated aqueous HCl, 10 ml THF, and 4.88 g $NH_2$-NHPh was cooled to 15° C. and 10.00 g 3,3-dimethoxy-2-dimethoxymethyl-propionate were fed within 5 minutes. The mixture was stirred at 20° C. for 3.0 hours after which a GC-analysis of the reaction mixture revealed complete conversion of the 3,3-dimethoxy-2-dimethoxymethyl-propionate. After cooling to room temperature, 6.73 g (74% of theory based on 3,3-dimethoxy-2-dimethoxyrnethyl-propionate) of methyl-1-phenyl-4-pyrazole-carboxylate was isolated as described in example 4. Identification of the product was based on $^1$H-NMR-, $^{13}$C- and IR-spectra. The mother liquor still contained methyl-1-phenyl-4-pyrazole-carboxylate.

EXAMPLE 7

Methyl-isoxazole-4-carboxylate

A stirred mixture of 4.96 g DI-water, 0.44 g concentrated aqueous HCl and 3.13 g NH$_2$OH was cooled to 15° C. and 10.00 g 3,3-dimethoxy-2-dimethoxymethyl-propionate were fed within 5 minutes. The initially biphasic, later on homogeneous reaction mixture, was stirred at 20° C. for 3.0 hours and subsequently worked-up as described in example 4. By this means, 4.02 g methyl-4-isoxazole4-carboxylate (92% of theory based on 3,3-dimethoxy-2-dimethoxymethyl-propionate) could be isolated. Identification of the product was based on $^1$H-NMR-, $^{13}$C- and IR-spectra.

EXAMPLE 8

Methyl-2-amino-pyrimidine-5-carboxylate

To a stirred solution of 4.30 g guanidine hydrochloride in 50.00 g dimethyl formamide, 10.00 g 3,3-dimethoxy-2-dimethoxymethyl-propionate were added. The resulting clear solution was heated to 100° C. for 2 hours and to 140° C. for an additional 20 hours. After cooling to 60° C., the solvent was completely removed in vacuo and the resulting light brown residue thoroughly extracted with boiling tetrahydrofurane. After distilling off the majority of the solvent, the crystalline product was isolated by suction filtration and subsequent drying in vacuo. A total of 4.34 g (63% of theory based on 3,3-dimethoxy-2-dimethoxymethyl-propionate) of methyl-2-amino-pyrimidine-5-carboxylate could be isolated in this way. Identification of the product was based on $^1$H-NMR-, $^{13}$C- and IR-spectra.

EXAMPLE 9

Methyl-3-keto-isoxazole-4-carboxylate-hydrochloride

To a stirred solution of 2.21 g methylhyroxylamine-hydrochloride in 2.90 g water and 0.26 g concentrated aqueous HCl, 5.81 g 3,3-dimethoxy-2-dimethoxymethyl-propionate were fed over a period of 40 minutes. External cooling with an ice-bath was required in order to keep the temperature between 15° C. and 20° C. After stirring for an additional 15 minutes and cooling to 10° C., a non-stirrable white crystal-pap was gained. The needle-shaped crystals were isolated by suction-filtration, washing with a small amount of diisopropylether and drying in vacuo. Further product-fractions could be isolated by evaporation of part of the mother liquor, filtration, washing, and drying. The total amount of methyl-3-keto-isoxazole-4-carboxylate-hydrochloride obtained in this way was 4.60 g (91% theory based on 3,3-dimethoxy-2-dimethoxymethyl-propionate). Identification of the product was based on $^1$H-NMR-, $^{13}$C- and IR-spectra. The $^1$H-NMR-spectrum did not show any impurities.

What is claimed is:
1. A process for preparing pyrazoles, isoxazoles and pyrimidines of general formula I, II, III and IV:

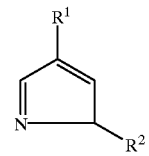

I

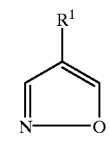

II

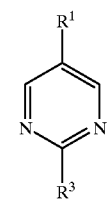

III

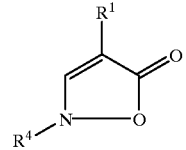

IV in which $R^1$ represents COOH, COONa, COOR, CHO, C(OR)$_2$, CN, CONH$_2$, CONHR or CONR$_2$, in which $R^2$ represents H, an alkyl-, cycloalkyl, aralkyl- or aryl-group with up to 12 carbon atoms, COOR, CONH$_2$, CONHR, CONR$_2$, alkyl-OH, cycloalkyl-OH, aralkyl-OH, aryl-OH, alkyl-OR, cycloalkyl-OR, arakyl-OR and aryl-OR, in which $R^3$ represents H, an alkyl-, cycloalkyl-, aralkyl- or aryl-group with up to 12 carbon atoms, OH, OR, SH, SR, NH$_2$, NHR and NR$_2$, NHNO$_2$, NHNH$_2$, NHNHR, NHNR$_2$, COOR, CONH$_2$, CONHR, CONR$_2$, in which $R^4$ represents an alkyl-, cycloallyl-, aralkyl- or aryl-group with up to 12 carbon atoms, wherein 2-substituted acetals of malondialdehyde of general formula VI:

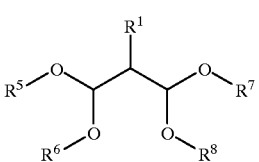

VI in which $R^1$ represents COOH, COONa, COOR, CHO, C(OR)$_2$, CN, CONH$_2$, CONHR or CONR$_2$, and in which $R^5$, $R^6$, $R^7$ and $R^8$ are the same or different alkyl-, cycloalkyl-, aralkyl- or aryl-groups with up to 12 carbon atoms, are reacted with one or several reactants selected from the group consisting of hydroxylamines and their salts, hydrazines and their salts, formamid, amidines and their salts, guanidines and their salts, aminoguanidines and their salts, nitroguanidine and their salts, O-alkyl-isoureas and their salts, O-cycloalkyl-isoureas and their salts, O-aralkyl-isoureas and their salts, O-aryl-isoureas and their salts, S-alkyl-isothioureas, S-cycloalkyl-isothioureas, S-aralkyl-isothioureas, S-arylisothioureas, S-alkyl-isothiouronium salts, S-cycloalkyl-isothiouronium salts, S-aralkyl-isothiouronium salts, S-aryl-isothiuronium salts, thiourea and urea.

2. The process of claim 1, wherein the compounds of general formula VI are fed to the rest of the reaction mixture.

3. The process of claim 1, wherein the reaction is carried out in the presence of at least catalytic amounts of water.

4. The process of claim 1, wherein the reaction is carried out in the presence of a co-solvent.

5. The process of claim 1, wherein the reaction is carried out in the presence of a polar solvent.

6. The process of claim 1, wherein the reaction is carried out in the presence of a polar solvent that does not react to a significant extent with any other component of the reaction mixture.

7. The process of claim 5, wherein the polar solvent is selected from the group consisting of an ether, cyclic ether, polyethylenglycol ether, a dialkyl amide, or DMSO.

8. The process of claim 1, wherein the product that is formed from the malondialdehyde acetal of general formula VI and the reactants is used as the solvent.

9. The process of claim 1, wherein the reaction is catalyzed by an acidic catalyst.

10. The process of claim 9, wherein the acidic catalyst is selected from the group consisting of HCl, $H_2SO_4$, acidic ion exchange resins, or acidic aluminum oxide.

11. The process of claim 1, wherein the alcohols of general formula $R^5OH$, $R^6OH$, $R^7OH$ and $R^8OH$ are removed during the reaction.

12. The process of claim 11, wherein the alcohols are removed by distillation.

13. The process of claim 12, wherein the alcohols are removed continuously.

14. The process of claim 1, which comprises reacting the products of general formula I, II, III and IV are isolated in the form of acidic salts.

15. The process of claim 14, wherein the products of general formula I, II, III and IV as hydrochlorides.

16. The process of claim 1, wherein the reaction is carried out continuously.

17. The process according to claim 1, wherein the groups $R^5$, $R^6$, $R^7$ and $R^8$ are identical.

* * * * *